US00PP35686P2

(12) United States Plant Patent
Horvath

(10) Patent No.: US PP35,686 P2
(45) Date of Patent: Mar. 12, 2024

(54) ***VERONICA* PLANT NAMED 'SEASIDE'**

(50) Latin Name: ***Veronica* hybrid**
Varietal Denomination: Seaside

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 17/803,984

(22) Filed: Feb. 16, 2023

(51) Int. Cl.
*A01H 5/02* (2018.01)
*A01H 6/68* (2018.01)

(52) U.S. Cl.
USPC ..... Plt./251
CPC ..... *A01H 6/68* (2018.05)

(58) Field of Classification Search
USPC ..... Plt./251
CPC ..... A01H 6/68; A01H 5/02
See application file for complete search history.

*Primary Examiner* — Keith O. Robinson

(57) ABSTRACT

A new, distinct *Veronica* plant as described and illustrated, characterized by the combination of longer and wider foliage and longer and wider blue flower spikes.

1 Drawing Sheet

Figure 1:
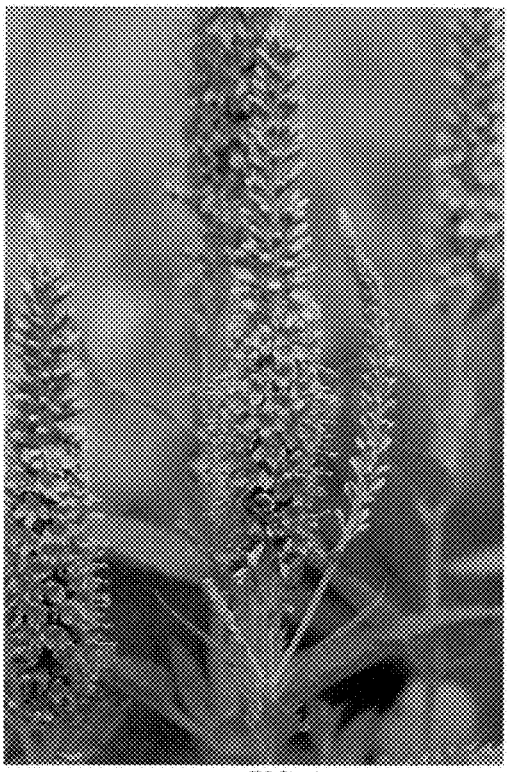

Latin name: *Veronica* hybrid.
Cultivar name: 'Seaside'.

BACKGROUND OF THE INVENTION

The present invention relates to a new and distinct hybrid of *Veronica* plant named 'Seaside' characterized by the combination of longer and wider foliage and longer and wider blue flower spikes, compared to the seed parent. The new *Veronica* was raised as a seedling from open pollinated seed sown from the seed parent *Veronica* x 'Kiss the Sky' U.S. Plant Pat. No. 31,665, patented, in Hebron, IL in 2016. The male, pollen parent is unknown and the new plant was selected as a chance seedling. The selection of the new plant was due to the combination of longer and wider foliage and longer and wider blue flower spikes compared to the seed parent. Initial asexual reproduction has taken place at a nursery in Hebron, IL since 2017 by means of division, and vegetative stem cuttings. Continued asexual propagation by division and vegetative stem cuttings since that time has shown that the unique features of the new *Veronica* plant are stable and reproduced true to type in successive generations. No plants of the new *Veronica* have been sold in this country, or anywhere in the world, prior to the filing of this application, nor has any disclosure of the new plant been made prior to the filing of this application with the exception of that which was disclosed by the inventor and his nursery, in Hebron, IL. As well as licensees who did obtain plants from the inventor within one year of filing of this application and was derived directly from the inventor.

SUMMARY OF THE INVENTION

The new *Veronica* plant named 'Seaside' characterized by combination of longer and wider foliage and longer and wider blue flowers compared to the seed parent have been observed to be unique and stable. For purpose of comparison the new plant will be referred to as 'Seaside'.

Plants of 'Seaside' can be compared to the seed parent plant of *Veronica* x 'Kiss the Sky' U.S. Plant Pat. No. 31,665. 1. Plants of 'Seaside' inflorescence grows to 33 cm in length while *Veronica* x 'Kiss the Sky' has an inflorescence growing to 29 cm in length. 2. Plants of 'Seaside' foliage grows to 11 cm in length and 4 cm in width while *Veronica* x 'Kiss the Sky' has foliage grows to 8-10 cm in length and 3.5 cm in width. 3. Plants of 'Seaside' foliage color is 135 B while *Veronica* x 'Kiss the Sky' foliage color is 137 A.

Plants of 'Seaside' can be compared to plants of *Veronica* x 'Spike' U.S. Plant Pat. No. 27,814. 1. Plants of 'Seaside' inflorescence grows to 33 cm in length while *Veronica* x 'Spike' has an inflorescence growing to 23 cm in length. 2. Plants of 'Seaside' grows to 90 cm tall while *Veronica* x 'Spike' grows to 40 cm tall. 3. Plants of 'Seaside' foliage color is 135 B while *Veronica* x 'Spike' foliage color is 139 A.

Plants of 'Seaside' can be compared to plants of *Veronica* x 'Pure Silver', not patented. 1. Plants of 'Seaside' inflorescence grows to 33 cm in length while *Veronica* x 'Pure Silver' has an inflorescence growing to 10 cm in length. 2. Plants of 'Seaside' grows to 90 cm tall while *Veronica* x 'Pure Silver' grows to 40 cm tall. 3. Plants of 'Seaside' foliage color is 135 B while *Veronica* x 'Pure Silver' foliage color is silver.

DESCRIPTION OF PHOTOGRAPHS

Figure 2:
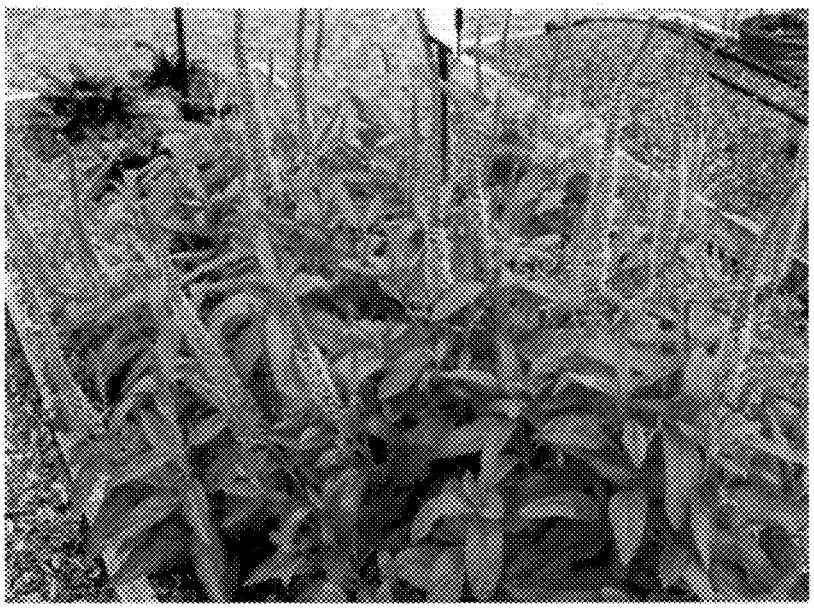

Plants pictured in the drawing were grown for one year.
FIG. 1. Close up of the flower spike.
FIG. 2. A mature plant.

DETAILED BOTANICAL DESCRIPTION

In the following description, color references are made to The Royal Horticultural Society Colour Chart (2001). Plants used for the description were grown for one year at a nursery in Hebron, Illinois. Measurements and numerical values represent averages of typical plants.

Plant:

*Botanical classification.*—*Veronica* hybrid.

*Parentage.*—Female (seed parent) *Veronica* x 'Kiss the Sky', Male parent, unknown.

*Form.*—Upright.
*Plant height.*—90 cm from soil to top of flowers; width: 60 cm wide.
*Growth.*—Herbaceous perennial, upright, good vigor.
*Roots.*—Fibrous.

Stem:
*Form.*—Cylindrical, branching from the base, no pinching required.
*Color.*—143 A.
*Surface texture.*—Glabrous.
*Length.*—90 cm. Strength. — Strong.
*Diameter.*—5 mm wide.
*Flower stem internode length.*—4-5 cm.
*Internode quantity.*—Typically 6.

Foliage:
*Arrangement.*—Opposite.
*Number of leaves per basal stem.*—12, 6 pairs.
*Size of leaf.*—Length: 11 cm on average, decreasing in both length and width distally. Width: 4 cm.
*Shape of leaf.*—Lanceolate.
*Shape of tip.*—Acute.
*Shape of base.*—Rounded to slightly attenuate.
*Texture of upper and lower surfaces.*—Glabrous.
*Margin type.*—Serrate.
*Color.*—Young leaves upper surface: close to 135 B. Lower surface: 135 C Mature leaves: Upper surface: 135 B. Lower surface: close to 135 B.
*Petioles.*—Glabrous. Length: 30 mm on average for lower leaves; 5 mm on average for other leaves. Diameter: 2 mm. Color: Adaxial 135 B, Abaxial between 135 B and C. Surface: Adaxial glabrous, Abaxial glabrous. Strength: strong.
*Veins.*—Pattern: Pinnate with a pronounced mid-vein on the lower surface and depressed on the upper leaf surface. Color: Upper surface: 135 B. Lower surface: 135 B.

Flower:
*Natural flowering season.*—Continuous from mid to late July into August.

Inflorescence type and habit: Branched, terminal spike, no fragrance, flowers last about 7 days on plant. Rate of flower opening: About 25% of flowers open at once, all flowers open in about 4 weeks.

Type of flower: Tubular with four petal lobes.

Number of flowers: About 120 per spike; about 60 per lateral branch.

Inflorescence size:
*Diameter of an inflorescence.*—25-30 mm. Height. — 33 cm.
*Length of terminal spike.*—33 cm.
*Individual flower size.*—7 mm long, 8 mm wide.
*Diameter of an individual flower.*—8 mm. Length of an individual flower — 7 mm.
*Diameter of an individual flower throat.*—3 mm.
*Diameter of the flower tube.*—3 mm. Length of the flower tube — 5 mm.

Peduncle:
*Length.*—11 cm. Diameter. — 2 mm.
*Color.*—143 A.
*Orientation.*—Upright with 4-5 secondary peduncles at 30-45°.
*Strength.*—Strong.
*Surface.*—Glabrous.

Pedicel: Length. — 1-2 mm long, less than 1 mm wide. Color. — 134 A.
*Surface.*—Adaxial glabrous, Abaxial glabrous. Strength: strong.

Petals:
*Petal arrangement.*—One larger above three slightly smaller.
*Large petal size.*—8 mm long; 5 mm wide. Small petal size. — 8 mm long; 3 mm wide.
*Margin.*—Entire.
*Petal shape.*—Oblanceolate.
*Tip shape.*—Emarginate upper lip; rounded lower lip.
*Length.*—Average upper lip: 4 mm; average lower lip: 3 mm.
*Width.*—Average upper lip: 5 mm; average lower lip: 3 mm.
*Petal quantity.*—4.
*Petal texture of upper and lower surfaces.*—Glabrous.
*Corolla.*—Length: 5 mm long, width: 3 mm wide, Color: 97 A.
*Petals.*—When opening: Upper surface: 97 A. Lower surface: 97 A. Fully opened: 97 A. Lower surface: 97 A.

Bud:
*Shape.*—Convolute, narrowly oblong, obtuse apex.
*Length.*—5 mm. and Diameter. — 2 mm. Color — 97 A.

Calyx:
*Arrangement.*—4 free sepals.
*Height.*—3-4 mm.
*Diameter.*—2 mm.
*Shape.*—Free.
*Sepals.*—Quantity 4. Shape: ovate, acute apex, base fused forming corolla., Size: Average 4 mm long; 1-2 mm wide. Margin: Entire. Texture of upper and lower surfaces: glabrous. Color: Outer surface: 97 A. Inner surface: 97 A.
*Bracts.*—None observed.

Reproductive organs:

Stamens:
*Number.*—2.
*Filament length.*—11 mm.
*Anthers.*—Shape: Basffixed, elliptic. Length: 2 mm. Width 1 mm. Color: 85 B.
*Pollen.*—Color: white 155 C Amount: low.

Pistil:
*Number.*—One. Length. — 8 mm, less than 1 mm wide.

Style-Length: 8 mm. Color: 97 B at the top half fading to white 155 C at the base.

Stigma-Shape: cylindrical. Color: 97 B. Ovary color: N77 C and 147 C at the base.

Seeds: Brown and round 2 mm long and 1 mm wide, color 200 B.

Disease/pest resistance: No unusual susceptibility to diseases or pests has been noted.

Temperature tolerance: Tolerate to heat at least up to 30° C. and cool at least down to USDA Zone 4-8.

I claim:

1. A new, distinct variety of *Veronica* plant named 'Seaside', substantially as described and illustrated, herein.

* * * * *